(12) United States Patent
Garidel et al.

(10) Patent No.: US 9,753,021 B2
(45) Date of Patent: Sep. 5, 2017

(54) METHOD FOR THE EVALUATION OF THE COLLOIDAL STABILITY OF LIQUID BIOPOLYMER SOLUTIONS

(71) Applicant: Boehringer Ingelheim International GMBH, Ingelheim Am Rhein (DE)

(72) Inventors: Patrick Garidel, Ingelheim Am Rhein (DE); Thomas Hennes, Ingelheim Am Rhein (DE); Torsten Schultz-Fademrecht, Ingelheim Am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 161 days.

(21) Appl. No.: 14/381,697

(22) PCT Filed: Feb. 27, 2013

(86) PCT No.: PCT/EP2013/053856
§ 371 (c)(1),
(2) Date: Aug. 28, 2014

(87) PCT Pub. No.: WO2013/131785
PCT Pub. Date: Sep. 12, 2013

(65) Prior Publication Data
US 2015/0015886 A1    Jan. 15, 2015

(30) Foreign Application Priority Data

Mar. 5, 2012    (EP) .................................... 12158026

(51) Int. Cl.
*G01N 33/15*    (2006.01)
*G01N 15/00*    (2006.01)
(Continued)

(52) U.S. Cl.
CPC ............. *G01N 33/15* (2013.01); *G01N 15/00* (2013.01); *G01N 21/85* (2013.01); *G01N 2015/0693* (2013.01); *G01N 2201/025* (2013.01)

(58) Field of Classification Search
CPC ................... G01N 21/85; G01N 33/15; G01N 2015/0693; G01N 15/06; G01N 2013/006;
(Continued)

(56) References Cited

U.S. PATENT DOCUMENTS 3,824,866 A * 7/1974 Schatz ................ B01F 11/0097
74/61
4,669,225 A * 6/1987 Kuster ................ B01F 11/0097
366/219

(Continued)

FOREIGN PATENT DOCUMENTS

WO    2004090383 A1    10/2004
WO    2013131785 A1    9/2013

OTHER PUBLICATIONS http://www.thefreedictionary.com/agitate.*
(Continued)

*Primary Examiner* — Tarifur Chowdhury
*Assistant Examiner* — Mohamed K Amara
(74) *Attorney, Agent, or Firm* — Paula K. Wittmayer; Atabak R. Royaee

(57) ABSTRACT

The invention concerns the field of biomolecule formulation screening and stability testing. It concerns a method for the evaluation of the colloidal stability of liquid biopolymer solutions. The present invention describes a method for determining the stability of a liquid pharmaceutical composition comprising: a) providing a liquid pharmaceutical composition in a container, b) shaking said container on a
(Continued)

shaker, whereby the shaker performs an oloid movement, c) determining the stability of said liquid pharmaceutical composition.

16 Claims, 5 Drawing Sheets

(51) Int. Cl.
*G01N 21/85* (2006.01)
*G01N 15/06* (2006.01)

(58) Field of Classification Search
CPC ......... G01N 21/359; G01N 2021/8592; G01N 21/3563; G01N 15/0205; G01N 21/64; G01N 21/59; G01N 21/6486; G01N 2021/4769; G01N 15/00; G01N 2201/025; B07C 5/342; B07C 5/3425; B07C 5/3427; G01J 3/42; G01J 3/2823; G01J 1/04; A61K 45/06
USPC ........................................................ 356/427
See application file for complete search history.

(56) References Cited

U.S. PATENT DOCUMENTS

| 4,784,338 | A | * | 11/1988 | Saladin | F16H 21/46 241/101.2 |
|---|---|---|---|---|---|
| 5,360,265 | A | * | 11/1994 | Cruse | B01F 11/0097 366/208 |
| 5,466,124 | A | * | 11/1995 | Dettwiler | B01F 11/0097 416/122 |
| 6,322,334 | B1 | * | 11/2001 | Klipstein | F01C 3/02 417/410.3 |
| 6,435,995 | B1 | * | 8/2002 | Salgo | F16H 7/00 474/148 |
| 7,670,043 | B2 | | 3/2010 | Fritschi | |
| 2006/0166612 | A1 | | 7/2006 | Fritschi | |
| 2007/0021929 | A1 | | 1/2007 | Lemmo | |

OTHER PUBLICATIONS https://vimeo.com/34543086 (Video Jan. 2012).*
http://biogenesislab.blogspot.com/2008/03/oloid-ag-basle-agitate-circulate-aerate.html (Schuran 2008).*
http://www.korallenriff.de/28interzoo/Schuran_04.html (Schuran2 2004).*
https://www.youtube.com/watch?v=eRI3GU4QKTg (Video 2012).*
International Search Report and Written Opinion for corresponding application PCT/EP2013/053856, dated Jul. 2, 2013.
Sylvia Kiese et al: "Shaken, not stirred: Mechanical stress testing of an IgG1 antibody", Journal of Pharmaceutical Sciences, vol. 97, No. 10, (Oct. 1, 2008), pp. 4347-4366.

* cited by examiner

Triangle: shaking of formulation F1 with a horizontal shaker
Star : shaking of formulation F2 with a horizontal shaker
Diamond: shaking of formulation F1 with a oloid shaker
Rectangle: shaking of formulation F2 with a oloid shaker Movement in spatial direction y [a]

Rotation angle
360° = 2 Π ≈ 6.28

Movement in spatial direction z [a]

Rotation angle
360° = 2 Π ≈ 6.28

METHOD FOR THE EVALUATION OF THE COLLOIDAL STABILITY OF LIQUID BIOPOLYMER SOLUTIONS

BACKGROUND OF THE INVENTION

Technical Field

The invention concerns the field of biomolecule formulation screening and stability testing. It concerns a method for the evaluation of the colloidal stability of liquid biopolymer solutions. The present invention describes a method for determining the stability of a liquid pharmaceutical composition comprising: a) providing a liquid pharmaceutical composition in a container, b) shaking said container on a shaker, whereby the shaker performs an oloid movement, c) determining the stability of said liquid pharmaceutical composition.

Background

The overall stability of biopharmaceutical formulations depends on various stability parameters like colloidal stability at the water/air interface, ice/water interface or its chemical stability, just to name a few.

In the early development phase time-to-clinic is crucial to be able to show proof of clinical concept of the development candidate. Any upfront loading of development activities should be avoided.

An important aspect for the development of a liquid formulation/liquid biopolymer solution, especially a protein formulation, is its sensitivity against mechanical stress and its chemical or colloidal stability. To determine these key criteria of a liquid formulation/liquid biopolymer solution, especially of a protein formulation, different mechanical stress studies can be conducted like a shear force study, a freeze/thaw study or a shaking study. Especially in early development phases it is of importance to perform such studies in a short time period. The overall development goal is to realize a short time lines until start of the first clinical trials. New and improved testing and screening methods are needed to help in realizing the tight time schedules of early stage development phases. There is, therefore, a need to accelerate the development of suitable biopharmaceutical formulations, especially for liquid formulations/liquid biopolymer solutions, such as protein formulations.

SUMMARY OF THE INVENTION

As a solution the present invention surprisingly provides a method for shaking/testing/selecting a formulation such as a liquid biopolymer solution comprising a) providing such a liquid pharmaceutical composition/liquid formulation/liquid biopolymer solution in a container, and b) shaking said container on a shaker, whereby the shaker performs an oloid movement. The method of the present invention is a very fast screening method to determine the colloidal stability of the liquid biomolecule formulations due to the use of an oloid shaker.

The present invention (=BI-Intromix™) is a key contribution to shorten development time lines for the selection of colloidal stable formulations. The present invention (BI-Intromix™) is a new application for carrying out shaking studies using a very specific shaking design.

The essence of this invention is the special movement regime which is used for shaking the liquids such as liquid protein formulations.

The exceptional efficiency of the shaker/mixer comes from the use of a sophisticated oloid movement. The oloid movement consists of several elliptical rotations. The container containing the liquid formulation/biopolymer solution is set into three-dimensional movement that exposes the liquid protein formulations to always changing, rhythmically pulsing motion (see FIG. 1). The oloid movement can be described as the addition of a translation and rotation movement resulting in an inversal movement (Dirnböck et al., Journal for Geometry and Graphics Volume 1 (1997), No. 2, 105-118). Characteristic for the oloid movement is its rhythmical pulsation which generates a very high shaking intensity compared to other shaking methods like the horizontal movement shaker. Because of the higher shaking intensity it is possible to accelerate a shaking study from 1 or several weeks depending on the stability of the protein to durations of 24 hours or less down to 3 hours.

The method of this invention can be conducted with any kind of container like vials, syringes, carpules or bags. To perform the method of the present invention (for performing stress studies) the container is fixed into a kind of cage and the cage executes the oloid movement to give mechanical stress into the protein solution.

The method of this invention allows a high throughput screening for exploring the shaking stability of a high number of samples with varying liquid formulations during formulation finding such as e.g. protein pre-formulation.

The sensitivity of the testing/shaking method can be determined using a turbidity assay. The increase of the turbidity (see FIG. 2) is much higher for the oloid shaker compared to the horizontal shaker, which correlates with a higher sensitivity and a reduced shaking time of the method of the present invention in comparison to standard (e.g. horizontal) shaking tests.

Figure 1A:
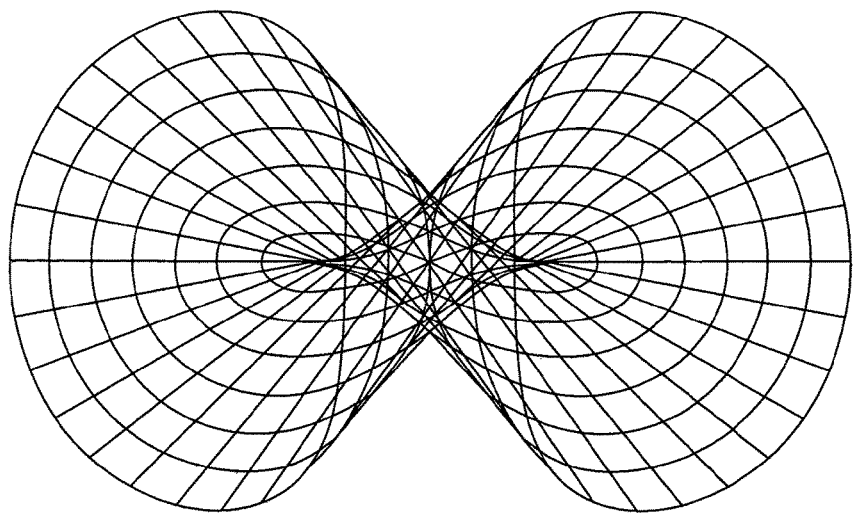
FIG. 1.

A) Schematic of the sophisticated oloid movement consisting of several elliptical rotations.

B) Two disks of radius r intersect one another perpendicularly and have a diameter in common. If the distance of two centers of disks is equal to the radius, then the convex hull produces a figure that rolls smoothly and is known as the oloid (Schatz, P. "Das Oloid als Wälzkörper." §14 in Rythmusforschung and Technik. Stuttgart: Verlag Freies Geistesleben, 1975, p. 122; Nishihara, http://www1.ttcn.ne.jp/~a-nishi/oloid/z_oloid.html). From http://mathworld.wolfram.com/Oloid.html.

C) A six-link spatial mechanism; from V. Brat, A six-link spatial mechanism, Jnl. Mechanisms Vol 4, pp 325-336, 1969

FIG. 2:

Measurement of the turbidity in dependency of the process time. The turbidity was determined by measuring the scattering intensity of the solution using a light beam with a wavelength of 633 nm and a scattering angle of 90 degree. In the diagram the two different kinds of mechanical or shaking stress are compared using an oloid shaped movement and a horizontal shaped movement.

Triangle: shaking of formulation F1 with a horizontal shaker

Star: shaking of formulation F2 with a horizontal shaker

Diamond: shaking of formulation F1 with a oloid shaker

Rectangle: shaking of formulation F2 with a oloid shaker

FIG. 3:

Movement of the center of mass of the "Probentrommel" (drum containing the container/cage, where the container is fixed to) A), B) and C): movement of the x, y and z axis of the center of mass/gravity of the "Probentrommel" (e.g. drum containing the container or the cage, where the container is fixed to)

D) to E) figure-of-eight movement of the center of mass/gravity

Figures were generated using "Mathematica®".

See also FIGS. 5 and 6 and equation (21) from V. Brat, A six-link spatial mechanism, Jnl. Mechanisms Vol 4, pp 325-336, 1969, where the author describes the movement of the center of mass of the "Probentrommel" (drum containing the container/cage, where the container is fixed to).

DETAILED DESCRIPTION OF THE INVENTION

One important aspect for the development of a liquid protein containing formulation is the prevention of protein aggregation induced by e.g. shear stress, shaking stress, thermal stress or the like. For the evaluation of the behavior of a protein against stress it's very common to prove its sensitivity by carrying out stress studies like a storage stability study at elevated temperature, e.g. 40° C. or shaking studies. One other important aspect especially in early development phases is to realize a short time to clinic for clinical phases 1 or 2. Therefore it's necessary to have meaningful and fast development tools for the formulation development.

Furthermore it is an advantage to prove stress parameters, which are realistic or which can occur during the life cycle from manufacturing of the drug product until administration to the patient. Therefore, it is necessary to carry out a storage stability study of a protein formulation at different temperatures. Stress on the drug product can also happen during shipment particularly due to shaking of the product. In addition, the stress conditions during shipment are very important to understand because the way of the drug product after manufacturing to the patient can take several days up the weeks. This means also that the drug product can be exposed to stress over the duration of the shipment. Altogether, a shaking stress study is a mandatory tool for a successful formulation development.

Firstly, during shaking (e.g. during transport) protein aggregation can occur due to protein denaturation at hydrophobic surfaces or layers like glass, plastic, ice or air. Because of the relative movement of the liquid in relation to the container the liquid surface, especially at the interface air/liquid, is rebuilt continuously. Consequently the denaturation rate is accelerated at this interface.

Secondly, based on shaking, shear forces into the liquid can built up, which result in protein denaturation or aggregation (van der Veen et al., Biotechnol. Prog. 2004, 20, 1140-1145). Nevertheless Bee et al. (Biotechnol Bioeng. 2009 Aug. 1; 103 (5): pp. 936-943) examined the influence of shear forces on the denaturation of proteins and assumed that the forces on the protein are small compared to the forces acting at the air/liquid interface, because of the shear gradient, and therefore this factor can be assumed to be negligible.

For assessing the protein sensitivity against denaturation at hydrophobic layers different techniques are mentioned in the literature. Mahler et al. (European Journal of Pharmaceutics and Biopharmaceutics 59 (2005) 407-417) described the aggregation of IgG1 after stirring or after shaking. The protein solutions were exposed to shaking stress using a horizontal movement of a shaking plate with 150 amplitudes per minutes. In comparison to this the liquids were stirred using small reaction vials and Teflon coated stirring bars. The magnetic stirrer was adjusted to 600 rounds per minutes. Both methods showed a protein aggregation after 48 h depending on the used protein formulation.

Kiese et al. described the effects of shaking stress and stirring on antibodies using a horizontal shaker and a magnetic stirrer (Kiese et al., Journal of Pharm. Sc. Vol 97, No 10, October 2008). The duration of the stress given to the system was up to 7 days. As a result is was found that both stress methods induced protein aggregation and particle formation depending on the protein formulation.

However, the mechanical stress studies described above have several disadvantages:

Mechanical stress studies using stirred liquids have the disadvantage that this kind of mechanical stress won't occur until after the fill and finish process of the drug product and therefore the results are not transferable to the storage stability of the drug product.

Furthermore, it has been found that the damage pattern of the protein is different depending on the used mechanical stress method. Consequently, a direct correlation is not possible using the prior art methods.

Furthermore, as mentioned above the degradation profile of a stirred liquid is not identical to the related profile after shaking.

Another issue especially for studies using a horizontal shaker is that it is a time consuming procedure.

However, these shaking studies of the prior art work only well for very shaking sensitive proteins. Very shaking sensitive proteins produce interpretable results for a formulation finding within an acceptable shaking time of about 48 hrs. In most cases, however, the proteins show no degradation within this time period of 48 h. Consequently, the duration of the stress studies using conventional methods has to be prolonged to 1 or more weeks.

The present invention circumvents the above described disadvantages. Because of the very intensive and effective shaking procedure based on the special oloid movement regime the process time can be reduced to 24 hours or less compared to the related shaking studies using a horizontal shaker. The tests can be carried out in the final container of the drug product with no other additional components such as stirring bars. Consequently, the degradation profile is not disturbed by additional surface interfaces.

Definitions

The general embodiments "comprising" or "comprised" encompass the more specific embodiment "consisting of". Furthermore, singular and plural forms are not used in a limiting way.

Terms used in the course of this present invention have the following meaning.

The term "oloid" describes a geometric object that was discovered by Paul Schatz (1898-1979) in 1929. An oloid is formed by taking the convex hull of the shape made by intersecting two disks of equal radius at right angles within one another, with the distance between the centers of the disks equal to their radius. The resulting convex hull is an oloid. For reference see for example Hans Dirnböck, Hellmuth Stachel (1997). "The Development of the Oloid". *Journal for Geometry and Graphics* 1:2, pp. 105-118 and Swiss patent CH500000.

The oloid is an octic surface (Trott, M. The Mathematica GuideBook for Graphics. New York: Springer-Verlag, pp. 1194-1196, 2004. http://www.mathematicaguidebooks.org/, pp. 1194-1196). For circles of radii a, the surface area of the resulting oloid is $A=4\pi a^2$. An oloid is a subject which causes a swaying movement, also called oloid movement.

An "oloid movement" can be described by the addition of a rotation and translation movement resulting in a pulsated transversal movement. Because of its pulsation and its transversal movements the intensity of shaking is very high. See for example http://en.wikipedia.org/wiki/Oloid and http://mathworld.wolfram.com/Oloid.html.

The terms "oloid movement" and "oloid motion" are used interchangeably.

The mathematics of the oloid movement are for example described in H. Stachel, Elemente der Mathematik, Band 29, Heft 2, pp 25-56, Mar. 10, 1974 and V. Brat, A six-link spatial mechanism, Jnl. Mechanisms Vol 4, pp 325-336, 1969. The V. Brath reference (V. Brat, A six-link spatial mechanism, Jnl. Mechanisms Vol 4, pp 325-336, 1969) is hereby included by reference.

Figure 1B:
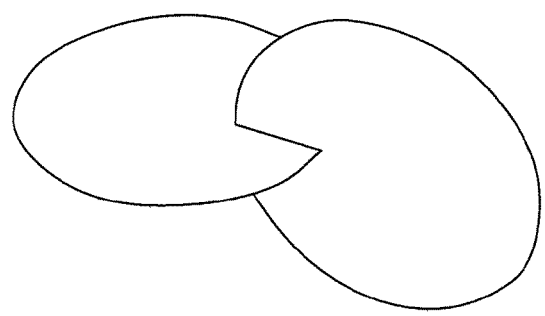
Figure 1C:
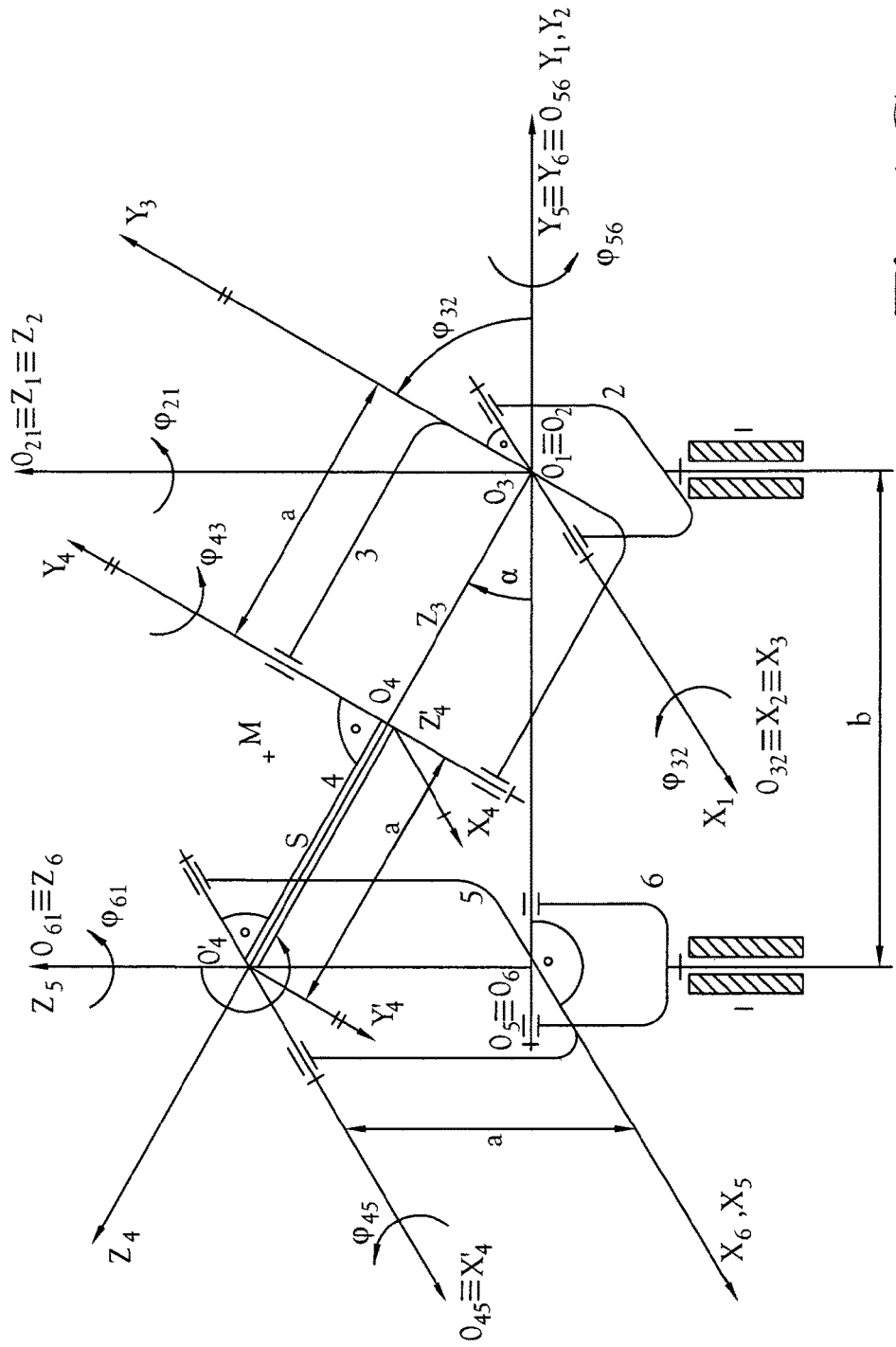

The author V. Brat describes the mathematics of oloid shakers/mixing drums performing the oloid movement. These oloid shakers or mixing drums employ a so called six-link spatial mechanism. Especially in equations (11) to (15) the author V. Brat describes the angles as a function of the rotation of the first angle phi21 ($=\phi_{21}$), which is the driving motor/driving member in the present invention. See also FIG. 1C (=FIG. 1 in document V. Brat).

$$\sin \phi_{32} = (\sqrt{3}/2)\cos \phi_{21} \quad \text{equation (11a)}$$

$$\cos \phi_{32} = (1/2)\sqrt{4-3\cos^2 \phi_{21}} \quad \text{equation (11b)}$$

$$\cos \phi_{56} = 1/\sqrt{4-3\cos^2 \phi_{21}},$$

$$\sin \phi_{56} = -\sqrt{3} \sin \phi_{21}/\sqrt{4-3\cos^2 \phi_{21}}; \quad (12)$$

$$\cos \phi_{45} = 1-(3/2)\cos^2 \phi_{21},$$

$$\sin \phi_{45} = -(\sqrt{3}/2)\cos \phi_{21}\sqrt{4-3\cos^2 \phi_{21}}; \quad (13)$$

$$\cos \phi_{43} = (3\cos^2 \phi_{21}-2)/(4-3\cos^2 \phi_{21}),$$

$$\sin \phi_{43} = -(2\sqrt{3})\sin \phi_{21}/(4-3\cos^2 \phi_{21}) \quad (14)$$

$$\cos \phi_{61} = \cos \phi_{21}/\sqrt{4-3\cos^2 \phi_{21}},$$

$$\sin \phi_{61} = -2 \sin \phi_{21}/\sqrt{4-3\cos^2 \phi_{21}}. \quad (15)$$

In equation (21) V. Brat describes the movement of the center of mass of the "Probentrommel" (e.g. drum containing the container or cage, where the container is fixed to). See therefore e.g. FIGS. 5 and 6 of the V. Brat reference or FIG. 3 of the present invention.

The parametric equation of the desired trajectory is obtained by introducing equations (11)-(15) into (20); the parameter is the rotation $\phi_{21}$ of the driving shaft.

The results are $$\begin{aligned} x_{s1} &= (a\sqrt{3}/8)\sin 2\varphi_{21}(2-3\cos^2\varphi_{21})/(4-3\cos 2\varphi_{21}) \\ y_{s1} &= (a\sqrt{3}/4)(3\cos^2\varphi_{21}-2\cos^2\varphi_{21}-4)/(4-3\cos 2\varphi_{21}), \\ z_{s1} &= (3a/4)(1+\sin^2\varphi_{21})/\sqrt{4-3\cos^2\varphi_{21}}. \end{aligned} \quad (21)$$

An "oloid shaker" is a shaker, which performs an oloid movement. The terms "oloid shaker" and "oloid mixer" are used interchangeably.

The term "pharmaceutical composition" describes a composition comprising a pharmaceutically active component and optionally further components such as buffer, salts, amino acids, saccharides, polyols or the like.

If substances have medicinal properties, they are considered "pharmaceuticals". A "pharmaceutical composition" is a composition comprising such a pharmaceutical or an active ingredient. A pharmaceutical composition may have various effects like antimicrobial activity, antiviral activity, anti-angiogenic activity, anti-tumor activity, activator or inhibitor or neutralizing function and many more. The pharmaceutical or active ingredient may have diverse and different chemical structures. Preferred within the meaning of the present invention are proteins and nucleic acids such as desoxyribonucleic acids and ribonucleic acids. The pharmaceutical composition usually comprises one or more excipients.

To be used in therapy, the pharmaceutical composition has to be appropriate to facilitate administration to animals or humans. Typically pharmaceutical compositions (=formulations) are prepared by mixing the pharmaceutical with physiologically acceptable carriers, excipients or stabilizers.

In the present invention such pharmaceutical compositions are preferably liquid such as high concentrated liquids/ high concentrated liquid formulations (HCLFs), aqueous solutions or aqueous and non-aqueous suspensions.

The term "liquid formulation" describes such a liquid pharmaceutical composition comprising a pharmaceutical together with one or more excipients.

Pharmaceutically acceptable carriers and adjuvants for use according to the present invention include, for example, ion exchangers, alumina, aluminum stearate, lecithin, serum proteins, buffer substances, water, salts or electrolytes and cellulose-based substances.

Carriers, excipients, modifiers or stabilizers are nontoxic at the dosages and concentrations employed. They include buffer systems such as phosphate, citrate, acetate and other anorganic or organic acids and their salts; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone or polyethylene glycol (PEG); amino acids such as glycine, glutamine, asparagine, histidine, arginine, or lysine; monosaccharides, disaccharides, oligosaccharides or polysaccharides and other carbohydrates, including glucose, mannose, sucrose, trehalose, dextrins or dextrans; chelating agents such as EDTA; sugar alcohols such as, mannitol or sorbitol; salt-forming counter-ions such as sodium; metal complexes (e.g. Zn-protein complexes); and/or ionic or non-ionic surfactants such as TWEEN™ (polysorbates), PLURONICS™ or fatty acid esters, fatty acid ethers or sugar esters. Also organic solvents can be contained in the pharmaceutical composition/formulation such as ethanol or isopropanol. The excipients may also have a release-modifying or absorption-modifying function. This is not a complete list of possible pharmaceutically acceptable carriers and adjuvants, and one of ordinary skilled in the art would know other possibilities, which are replete in the art.

A "biopolymer" is a polymer found in living cells, such as proteins or nucleic acids. The biopolymer consists of monomers. In the case of a protein these monomers are amino acids. In case of nucleic acids these monomers are bases or base pairs.

The term "liquid biopolymer solution" describes a biopolymer such as a protein or a nucleic acid in a liquid solution such as an aqueous one.

The term "protein" (used interchangeably with "polypeptide" and "amino acid residue sequence") refers to polymers of any amino acids (naturally occurring or artificial) of any length. The term "protein" includes also proteins that are post-translationally modified through reactions that include, but are not limited to glycosylation, glycation, acetylation, phosphorylation, oxidation, amidation or protein processing. Modifications and changes, for example fusions to other proteins, amino acid sequence substitutions, deletions or insertions, can be made in the structure of a polypeptide, preferably while the molecule maintains its biological functional activity. For example certain amino acid sequence substitutions can be made in a polypeptide or its underlying nucleic acid coding sequence and a protein can be obtained with like properties. Amino acid modifications can be prepared for example by performing site-specific mutagenesis or polymerase chain reaction mediated mutagenesis on its underlying nucleic acid sequence. The term "protein" or "polypeptide" thus also includes, for example, fusion proteins consisting of an immunoglobulin component, e.g. the Fc component, and a growth factor, e.g. an interleukin.

The term "protein" includes proteins, polypeptides, fragments thereof, and peptides, fusion proteins all of which can be expressed in host cell systems or synthesized via chemical methods. Desired proteins can be for example antibodies, enzymes, cytokines, lymphokines, adhesion molecules, receptors and derivatives or fragments thereof, and any other proteins or polypeptides that can serve as agonists or antagonists and/or have therapeutic or diagnostic use.

Desired proteins or polypeptides are for example (but not limited to): insulin, insulin-like growth factor, hGH, tPA, cytokines, such as interleukines (IL), e.g. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosis factor (TNF), such as TNF alpha and TNF beta, TNF gamma, TRAIL; G-CSF, GM-CSF, M-CSF, MCP-1, VEGF and single domain antibodies (e.g. derived from camelids). Also included is the production of erythropoietin or any other hormone growth factors and any other polypeptides that can serve as agonists or antagonists and/or have therapeutic or diagnostic use. The method according to the invention can also be advantageously used for formulation development/screening of antibodies, such as monoclonal, polyclonal, multispecific and single chain antibodies, or fragments thereof, e.g. Fab, Fab', F(ab')2, Fc and Fc'-fragments, heavy and light immunoglobulin chains and their constant, variable or hypervariable region as well as Fv- and Fd-fragments.

As used herein, the term "antibody" includes a polyclonal, monoclonal, bi-specific, multispecific, human, humanized, or chimeric antibody, a single chain antibody, an antigen-binding fragment of an antibody (e.g., an Fab or F(ab')$_2$ fragment), a disulfide-linked Fv, etc. Such antibodies may be produced through chemical synthesis, via recombinant or transgenic means, via cell (e.g., hybridoma) culture, or by other means.

Fab fragments (Fragment antigen-binding=Fab) consist of the variable regions of both chains which are held together by the adjacent constant region. These may be formed by protease digestion, e.g. with papain, from conventional antibodies, but similar Fab fragments may also be produced in the mean time by genetic engineering. Further antibody fragments include F(ab')2 fragments, which may be prepared by proteolytic cleaving with pepsin.

Using genetic engineering methods it is possible to produce shortened antibody fragments which consist only of the variable regions of the heavy (VH) and of the light chain (VL). These are referred to as Fv fragments (Fragment variable=fragment of the variable part). Since these Fv-fragments lack the covalent bonding of the two chains by the cysteines of the constant chains, the Fv fragments are often stabilized. It is advantageous to link the variable regions of the heavy and of the light chain by a short peptide fragment, e.g. of 10 to 30 amino acids, preferably 15 amino acids. In this way a single peptide strand is obtained consisting of VH and VL, linked by a peptide linker. An antibody protein of this kind is known as a single-chain-Fv (scFv). Examples of scFv-antibody proteins of this kind are known from the prior art.

In recent years, various strategies have been developed for preparing scFv as a multimeric derivative. This is intended to lead, in particular, to recombinant antibodies with improved pharmacokinetic and biodistribution properties as well as with increased binding avidity. In order to achieve multimerisation of the scFv, scFv were prepared as fusion proteins with multimerisation domains. The multimerisation domains may be, e.g. the CH3 region of an IgG or coiled coil structure (helix structures) such as Leucin-zipper domains. However, there are also strategies in which the interaction between the VH/VL regions of the scFv are used for the multimerisation (e.g. dia-, tri- and pentabodies). By diabody the skilled person means a bivalent homodimeric scFv derivative. The shortening of the Linker in an scFv molecule to 5-10 amino acids leads to the formation of homodimers in which an inter-chain VH/VL-superimposition takes place. Diabodies may additionally be stabilized by the incorporation of disulphide bridges. Examples of diabody-antibody proteins are known from the prior art.

By minibody the skilled person means a bivalent, homodimeric scFv derivative. It consists of a fusion protein which contains the CH3 region of an immunoglobulin, preferably IgG, most preferably IgG1 as the dimerisation region which is connected to the scFv via a Hinge region (e.g. also from IgG1) and a Linker region. Examples of minibody-antibody proteins are known from the prior art.

By triabody the skilled person means a: trivalent homotrimeric scFv derivative. ScFv derivatives wherein VH-VL are fused directly without a linker sequence lead to the formation of trimers.

The skilled person will also be familiar with so-called miniantibodies which have a bi-, tri- or tetravalent structure and are derived from scFv. The multimerisation is carried out by di-, tri- or tetrameric coiled coil structures. In a preferred embodiment of the present invention, the gene of interest is encoded for any of those desired polypeptides mentioned above, preferably for a monoclonal antibody, a derivative or fragment thereof.

There are also "scaffold proteins" or "scaffold antibodies" known in the art. Using this term, a scaffold protein means any functional domain of a protein, especially an antibody, that is coupled by genetic cloning or by co-translational processes with another protein or part of a protein that has another function.

The term "nucleic acid", "nucleic acid sequence", "nucleotide sequence", "polynucleotide", "polynucleotide sequence" as used herein refers to an oligonucleotide, nucleotide or polynucleotide and fragments and portions thereof and to DNA or RNA of genomic or synthetic origin, which may be single or double stranded and represent the sense or antisense strand. The sequence may be a non-coding sequence, a coding sequence or a mixture of both. A coding nucleic acid (e.g. "cDNA") in the context of this invention refers to deoxyribonucleic acids produced by reverse transcription and typically second-strand synthesis of mRNA or other RNA produced by a gene. If double-stranded, a cDNA molecule has both a coding or sense and a non-coding or antisense strand. The nucleic acid sequences of the present invention can be prepared using standard techniques well known to one of skill in the art. The "nucleic acid" may also be an antisense RNA, tRNA, rRNAs, other RNAs being part of riboproteins or other regulatory RNAs.

The term "stability" as used herein means prevention of aggregation, degradation, digestion, destruction such as mechanical destruction caused by shear stress or shaking, and the like. Stability mainly means the thermodynamic stability in a chemical system. Stability also means the preservation of the activity of the pharmaceutical comprised within the liquid pharmaceutical composition. Stability can be compromised by various factors such as temperature, mechanical stress or radiation.

Stability can be measured using various methods/assays. By applying chromatographically methods degradation products can be separated from the pharmaceutical composition/the intended biopolymer and can be detected by suitable detection techniques. In cases of proteins like antibodies typical chromatographical methods are the size exclusion chromatography, the hydrophobic interaction chromatography or the ion exchange chromatography. The detection of the degradation products can be realized e.g. by spectroscopic procedures like UV-detection or fluorescence detection. Further assays based on electrophoresis, like SDS-PAGE, nature PAGE, isoelectric focusing or capillary gel electrophoresis, are appropriate to determine a degradation of a liquid pharmaceutical composition/a biopolymer. Beside this the bioactivity of the liquid pharmaceutical composition/the biopolymer can be made accessible by specific bioassays or binding assay.

Beside these high sophisticated assays also other methods like the determination of turbidity, colour, visual particle, pH or the like can be used to evaluate the stability profile of a liquid containing a pharmaceutical composition/biopolymer, Special methods for determining the colloidal stability of liquids containing a pharmaceutical composition/biopolymer, especially proteins, are methods which determine the size of the biopolymer or the opalescence/turbidity of the solution. Hereby, typical analytical assays are size exclusion chromatography (SEC), SDS-PAGE, photo correlation spectroscopy (PCS), particle counting methods like light-obscuration or imaging methods (e.g. MFI™-method).

The determination of the turbidity can vary depending on the wavelength used or the scattering angle used. Commonly used wavelengths are 860 nm or the range between 400-600 nm. Related to the used calibration method the turbidity can be indicated in different units like FNU (Formazine Nephelometric Units) or NTU (Nephelometric Turbidity Units). Other units like FAU (Formazine Attenuation Units), FTU (Formazine Turbidity Units or TE/F (Trübungseinheit/Formazin) may be used as well, but are not really common for pharmaceutical purposes.

The term "colloidal stability" means a system in which the particles resist flocculation or aggregation and exhibits a long shelf-life. The "colloidal stability" will depend upon the balance of the repulsive and attractive forces that exist between particles as they approach one another. If all the particles have a mutual repulsion then the system will remain stable. However, if the particles have little or no repulsive force then some instability mechanism will eventually take place e.g. flocculation, aggregation etc.

The term "turbidity" means the cloudiness or haziness of a fluid caused by individual particles (suspended solids).

The terms "measuring" or "determining" are used interchangeably. The terms "measuring" or "determining" describe the quantification of one or more parameters (such as turbidity, conductivity or the like), which is or are indicative for a certain characteristic, feature or property, such as stability of the liquid pharmaceutical composition in the case of the method of the present invention.

Embodiments

The invention concerns a method for determining or measuring the stability of a liquid pharmaceutical composition or a liquid formulation or a liquid biopolymer solution comprising:
  a) providing a liquid pharmaceutical composition in a container,
  b) shaking said container on a shaker, whereby the shaker performs an oloid movement.
  c) determining or measuring the stability, preferably the colloidal stability, of said liquid pharmaceutical composition after shaking, e.g. by a turbidity assay.

The invention further relates to a method for conducting a mechanical stress study for a liquid pharmaceutical composition comprising:
  a) providing a liquid pharmaceutical composition in a container,
  b) shaking said container on a shaker, whereby the shaker performs an oloid movement.
  c) measuring/determining the stability of said liquid pharmaceutical composition after shaking, e.g. by a turbidity assay.

The invention describes a new and surprising method for conducting a mechanical stress study for pharmaceutical compositions/liquid formulations, especially of biopolymers/biomolecules, especially those containing proteins. The mechanical stress study consists of an accelerated shaking process having the attribute to be very efficient. This results in the outcome of a reduced process time.

The invention furthermore concerns a method for testing the stability of pharmaceutical compositions or for screening for a stable pharmaceutical composition comprising:
  a) providing a number of liquid pharmaceutical compositions in a/the same/number of containers,
  b) shaking said containers on a shaker, whereby the shaker performs an oloid movement,
  c) measuring/determining the stability, preferably the colloidal stability, of said liquid pharmaceutical composition after shaking, e.g. by a turbidity assay,
  d) selecting a stable liquid pharmaceutical composition.

The invention further relates to a method of selecting a stable pharmaceutical composition or of screening for a stable pharmaceutical composition comprising:
  a) providing a number of liquid pharmaceutical compositions in a number of containers,
  b) shaking said containers on a shaker, whereby the shaker performs an oloid movement,
  c) measuring/determining the stability, preferably the colloidal stability, of said liquid pharmaceutical compositions after shaking, e.g. by a turbidity assay,
  d) selecting a stable liquid pharmaceutical composition.

In a preferred embodiment of the testing/screening/selection methods described, the number of containers in step a) equals the number of liquid pharmaceutical compositions tested.

In another preferred embodiment of the testing/screening/selection methods described the number of liquid pharmaceutical compositions tested in step a) is at least 20, 50, 96, 100, 200, 384, 500 or 1000.

In a specific embodiment of the above methods step c) comprises determining/measuring the colloidal stability of the liquid pharmaceutical composition. In a further specific embodiment of the above methods step c) comprises measuring/determining the turbidity of the liquid pharmaceutical composition. Preferably, turbidity of said liquid pharmaceutical composition is measured by using a particle counting method such as light obscuration or an imaging method, or alternatively by using photo correlation spectroscopy (PCS).

Preferably turbidity is measured/determined after 72 hrs or 48 hrs of shaking, most preferably after 24 hrs of shaking or less.

In another embodiment step b) is performed for 1 hr to 72 hrs, 1 hr to 48 hrs, 1 hr to 12 hrs or 1 hr to 6 hrs, preferably shaking in step b) is performed for 3 hrs to 24 hrs.

In a further embodiment shaking step b) is performed for no longer than 72 hrs, 48 hrs, 24 hrs, 12 hrs, 9 hrs or 6 hrs.

In another embodiment shaking step b) is performed for less than 72 hrs or less than 48 hrs or less than 12 hrs or less than 6 hrs.

In a preferred embodiment step c) is performed after 48 hrs or less of shaking, preferably after 24 hrs, 12 hrs, 6 hrs or less of shaking, most preferably between 3 to 24 hrs of shaking.

In another embodiment said liquid pharmaceutical composition contains a desoxyribonucleic acid, a ribonucleic acid or a protein.

In a preferred embodiment the liquid pharmaceutical composition comprises a protein.

In a further preferred embodiment the protein is an antibody.

In another embodiment the liquid pharmaceutical composition comprises a desoxyribonucleic acid.

In a further embodiment the liquid pharmaceutical composition comprises a ribonucleic acid.

In another embodiment said liquid pharmaceutical composition/liquid formulation/liquid biopolymer solution is a protein formulation, preferably an antibody formulation.

In a specific embodiment the container of step a) contains a volume of 20 ml or less, preferably 10 ml, 5 ml, 2 ml, 1 ml, 0.5 ml, 0.2 ml or 0.1 ml or preferably between 0.1 ml to 10 ml. In a further specific embodiment the container of step a) contains a volume of 100 ml, 150 ml or 200 ml. A volume of 100 ml (or 150 ml or 200 ml) or 50 ml is specifically preferred in case the container is a bag.

In a further specific embodiment the container of step a) is a vial, syringe, carpule or bag.

In another embodiment the oloid movement in step b) is an addition of a translation and rotation movement resulting in an inversal movement.

In a specific embodiment the oloid movement in step b) is a three-dimensional movement that exposes the liquid pharmaceutical composition to always changing, rhythmically pulsing motion.

In a further embodiment the container of step a) is fixed into a kind of cage on the shaker of step b), and whereby the cage executes the oloid movement.

In another embodiment the container of step a) is the final container of the pharmaceutical composition. Hereby, final container means: exactly the container of the pharmaceutical composition, which is used for the application to a patient, without any other components. Final container further means: with no other/auxiliary components such as a stirring bar or the like.

Furthermore, from the shaking tests performed using the method of the present invention it can be concluded that the addition of surfactants like polysorbate 80 or polysorbate 20 stabilizes the liquid pharmaceutical compositions against shaking induced degradation, especially when containing a protein, preferably an antibody. Thus, the invention further relates to liquid pharmaceutical compositions stabilized by the addition of surfactants like polysorbate 80 or polysorbate 20. Preferably such liquid pharmaceutical compositions comprise a protein, preferably an antibody.

The practice of the present invention will employ, unless otherwise indicated, conventional techniques of pharmaceutical development, formulation development, chemistry, protein biology and the like which are in the skill of one in the art. These techniques are fully disclosed in the current literature.

The following examples are not limiting. They merely show possible embodiments of the invention. A person skilled in the art could easily adjust the conditions to apply it to other embodiments.

EXAMPLES

Example 1

An IgG4 antibody was mechanically stressed by using a horizontal shaker and by the procedure (oloid shaker) of the present invention. For the study 1 mL of different antibody formulations were filled in 2 mL Type 1 glass vials and closed with a rubber stopper. For the horizontal shaker the vials were fixed upside down to accomplish that all components of the vials including the rubber are in contact with the liquid. The shaking frequency was adjusted to 300 amplitudes per minutes. For the shaking procedure of the present invention the vials were fixed in a cage and mechanically stressed by an oloid-shaped movement. The frequency of the oloid shaped movement was adjusted to 67 rounds per minutes. The duration was 7 day for the horizontal shaker and 24 h for the oloid shaker. With this 2 shaking procedures a formulation screening was conducted using 6 different formulations. The table below listed the compositions of these formulations. The antibody concentration was adjusted to 10 mg/mL.

For the formulation screening the protein concentration measured by UV-spectroscopy, the turbidity and the monomer content measured by HP-SEC were conducted.

TABLE 1

| Batch No. | Protein concentration, | Buffer | Sugar | Surfactant |
|---|---|---|---|---|
| IgG4_F1 | 10 mg/mL | 25 mM Citrat, pH 6.0 | 200 mM Lactosucrose | 0.2 mg/mL polysorbate 20 |
| IgG4_F2 | 10 mg/mL | 25 mM Citrat, pH 6.0 | 200 mM Raffinose | 0.2 mg/mL polysorbate 20 |
| IgG4_F3 | 10 mg/mL | 25 mM Citrat, pH 6.0 | 200 mM Sucrose | 0.2 mg/mL polysorbate 20 |
| IgG4_F4 | 10 mg/mL | 25 mM Citrat, pH 6.0 | 200 mM Lactosucrose | — |
| IgG4_F5 | 10 mg/mL | 25 mM Citrat, pH 6.0 | 200 mM Raffinose | — |
| IgG4_F6 | 10 mg/mL | 25 mM Citrat, pH 6.0 | 200 mM Sucrose | — |

The results of the study were listed in the table 2. Using the oloid shaped movement regime it's possible to distinguish between the tested formulations of table 1. Overall without the addition of surfactant a protein damage occurs independent on the kind of added saccharide. Sucrose seems to be slight better compared to the other saccharides (lactosucrose, raffinose). Effects on the protein integrity could also be shown after 6 h shaking time. On the other hand after 7 days shaking time using the horizontal shaker no differences between surfactant containing and surfactant free formulations was obtained. In this case this method is not suitable getting results within 7 days with a consequence to prolong the study time.

TABLE 2

| Batch No. | | IgG4_F1 | IgG4_F2 | IgG4_F3 | IgG4_F5 | IgG4_F6 | IgG4_F7 |
|---|---|---|---|---|---|---|---|
| no mechanical stress | Turbidity, FNU | 4.7 | 4.9 | 5.0 | 4.0 | 4.8 | 4.9 |
| | Protein conc. mg/mL | 9.2 | 9.8 | 9.5 | 8.8 | 9.9 | 9.7 |
| | Monomer content, % | 99.5 | 99.3 | 99.5 | 99.4 | 99.4 | 99.4 |
| oloid shaking (6 h shaking time) | Turbidity, FNU | 46.9 | 5.3 | 20.4 | 4.0 | 4.6 | 4.8 |
| | Protein conc. mg/mL | nd | nd | Nd | nd | nd | nd |
| | Monomer content, % | 91.9 | 89.4 | 93.7 | 99.4 | 99.2 | 99.3 |
| oloid shaking (24 h shaking time) | Turbidity, FNU | 19.9 | 5.0 | 8.7 | 4.1 | 4.5 | 4.8 |
| | Protein conc. mg/mL | 2.8 | 3.7 | 5.6 | 8.9 | 10.0 | 9.8 |
| | Monomer content, % | 67.6 | 71.5 | 76.4 | 99.1 | 99.2 | 99.4 |
| horizontal shaking (1 day shaking time) | Turbidity, FNU | 7.3 | 4.7 | 4.9 | 4.1 | 4.5 | 4.9 |
| | Protein conc. mg/mL | nd | nd | nd | nd | nd | nd |
| | Monomer content, % | 99.3 | 99.1 | 99.3 | 99.4 | 99.2 | 99.4 |
| horizontal shaking (7 day shaking time) | Turbidity, FNU | 5.6 | 4.5 | 4.6 | 4.0 | 4.6 | 4.6 |
| | Protein conc. mg/mL | 9.5 | 10.0 | 9.7 | 8.7 | 9.9 | 9.8 |
| | Monomer content, % | 99.3 | 99.0 | 99.5 | 99.5 | 99.2 | 99.5 | nd = not determined

Example 2

Figure 2:
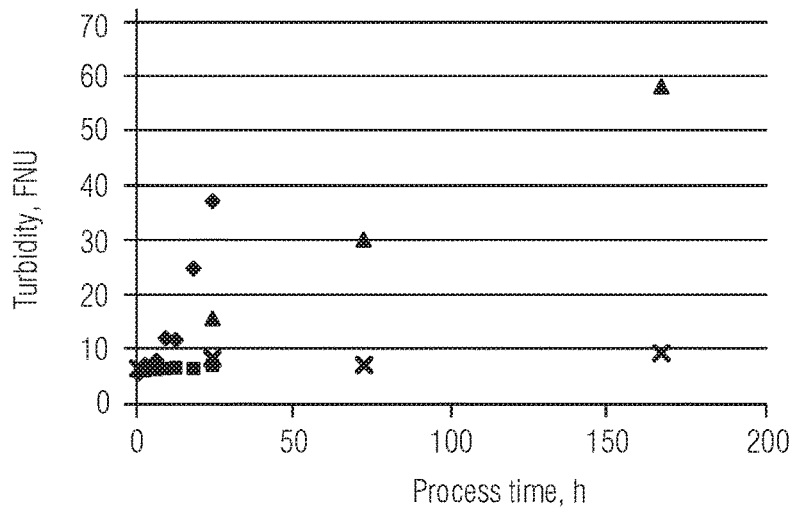
Figure 3A:
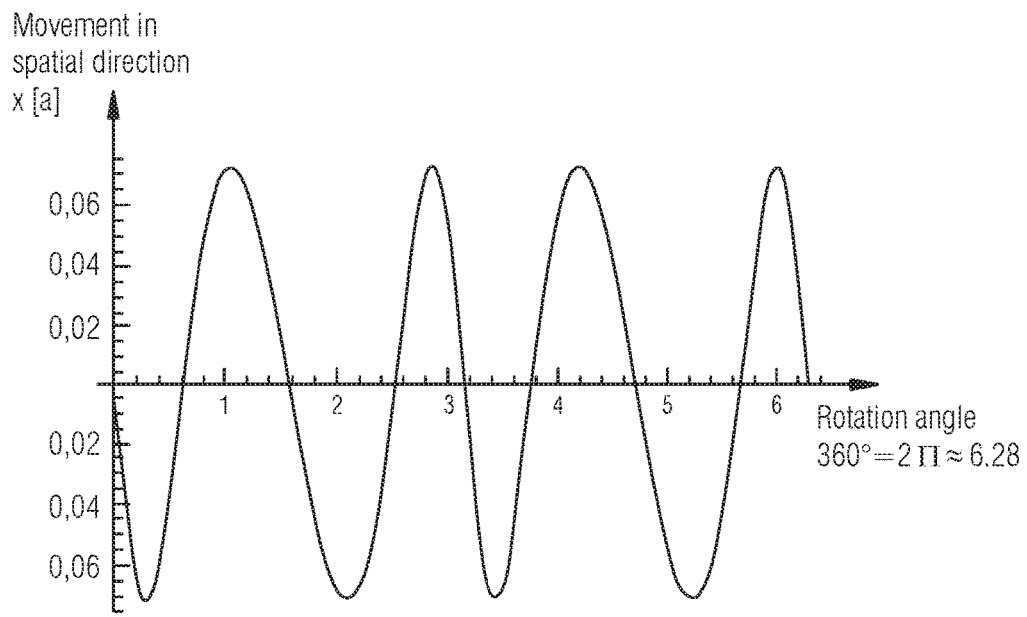
Figure 3B:
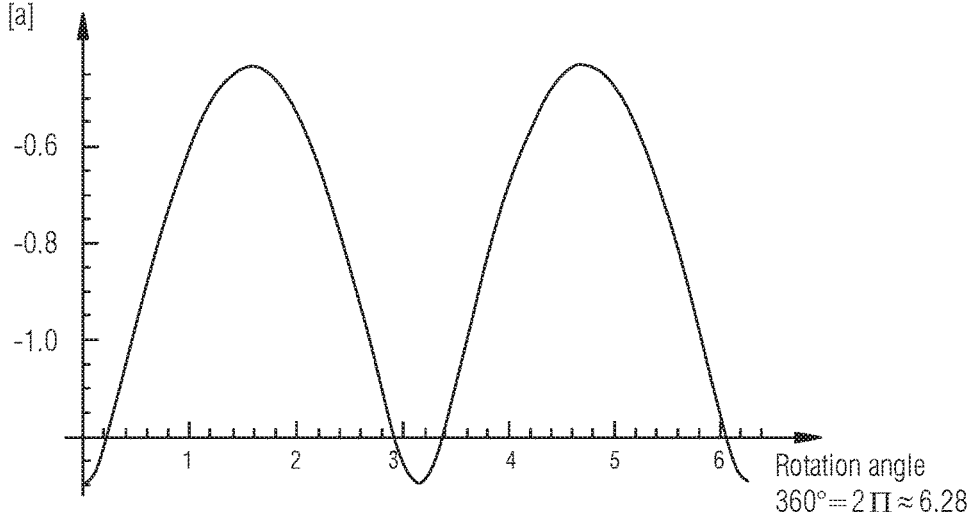
Figure 3C:
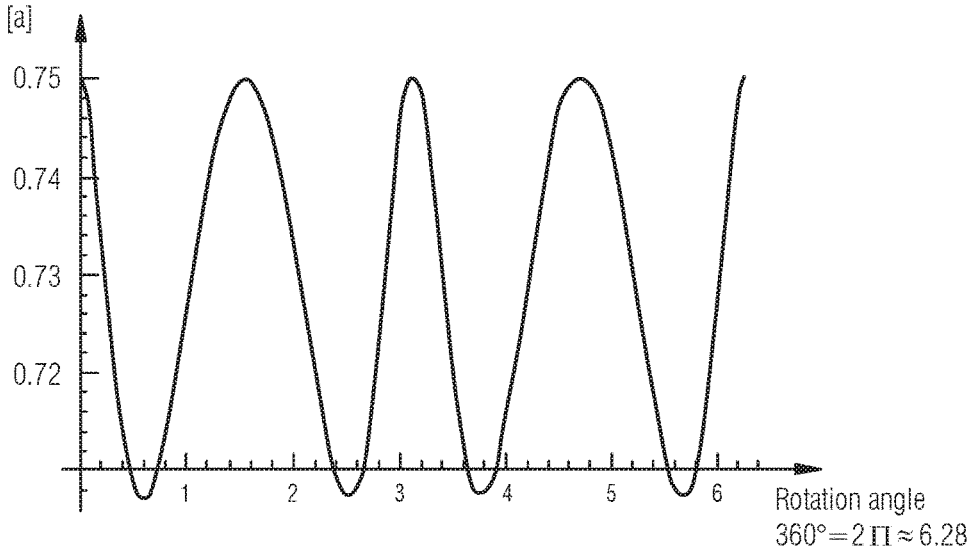
Figure 3D:
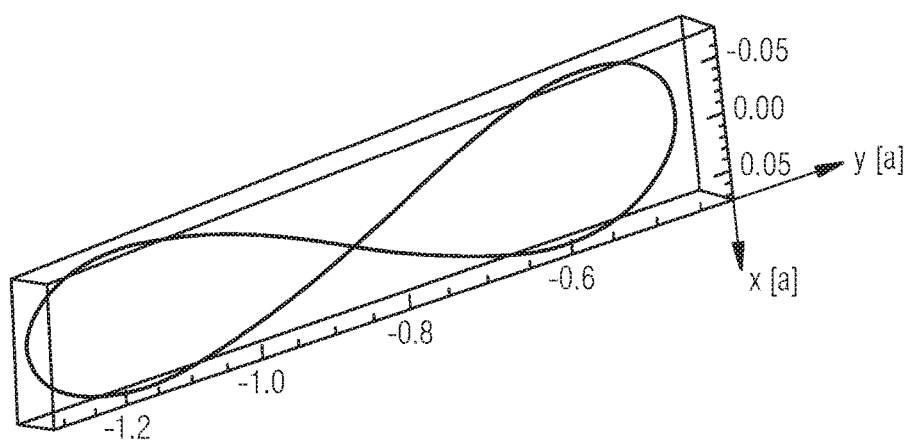
Figure 3E:
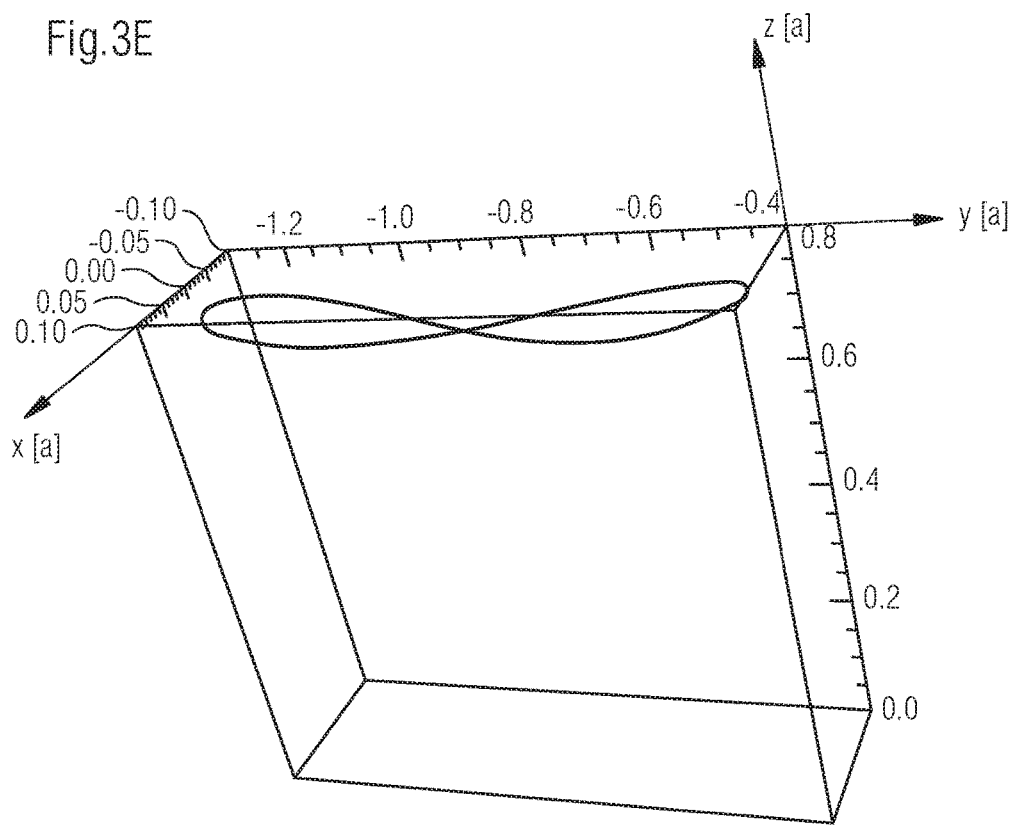

In this example an IgG1 antibody was mechanically stressed as described in example 1. The aim of the study was to compare shaking tests using a horizontal movement and an oloid movement regime. The shaking parameters were identical to the parameter mentioned in example 1. The tested formulations are listed in table 3. FIG. 2 shows the trend of the turbidity in dependence on the processing time. From both shaking tests it can be concluded that the addition of polysorbate 20 stabilizes the protein against shaking induced degradation. The increase of the turbidity is much higher for the oloid shaker compared to the horizontal shaker, which correlates with a higher sensitivity of the method and a reduced shaking time.

TABLE 3

| Batch No. | Protein concentration, | Buffer | Salt | Surfactant, mg/mL |
|---|---|---|---|---|
| IgG1_F1 | 10 mg/mL | 25 mM Citrat, pH 6.0 | 125 mM | 0.0 mg/mL |

TABLE 3-continued

| Batch No. | Protein concentration, | Buffer | Salt | Surfactant, mg/mL |
|---|---|---|---|---|
| IgG1_F2 | 10 mg/mL | 25 mM Citrat, pH 6.0 | 125 mM | 0.1 mg/mL Polysorbate 20 |

The invention claimed is:

1. A method for determining the stability of a liquid pharmaceutical composition comprising:
   a) providing a liquid pharmaceutical composition in a container,
   b) moving the said container in an oloid movement in three dimensions (x, y and z), wherein the oloid movement results in an increased turbidity of the liquid pharmaceutical composition, and wherein the increased turbidity is higher than a turbidity that would be produced by horizontal shaking of the container for a same amount of time, and
   c) determining the stability of said liquid pharmaceutical composition.

2. The method of claim 1, whereby step c) comprises determining the colloidal stability.

3. The method of claim 1, whereby step c) comprises determining the turbidity of said liquid pharmaceutical composition.

4. The method of claim 3, whereby turbidity of said liquid pharmaceutical composition is measured by using a particle counting method such as light obscuration or an imaging method, or alternatively by using photo correlation spectroscopy (PCS).

5. The method of claim 1, whereby step b) is performed for 1 hr to 72 hrs, 1 hr to 48 hrs, 1 hr to 12 hrs, 1 hr to 6 hrs, or 3 hrs to 24 hrs.

6. The method of claim 1, whereby step b) is performed for no longer than 72 hrs, 48 hrs, 24 hrs, 12 hrs, 9 hrs or 6 hrs.

7. The method of claim 1, whereby said liquid pharmaceutical composition contains a protein or a nucleic acid, whereby said nucleic acid is preferably a desoxyribonucleic acid or a ribonucleic acid.

8. The method of claim 1, whereby the liquid pharmaceutical composition comprises a protein.

9. The method of claim 8, whereby the protein is an antibody.

10. The method of claim 1, whereby the container of step a) contains a volume of 20 ml or less, preferably 10 ml, 5 ml, 2 ml, 1 ml, 0.5 ml, 0.2 ml or 0.1 ml or preferably between 0.1 ml to 10 ml.

11. The method of claim 1, whereby the container of step a) is a vial, syringe, carpule or bag.

12. The method of claim 1, whereby step b) includes a translation and rotation movement resulting in an inversal movement.

13. The method of claim 1, whereby the container of step a) is fixed into a kind of cage whereby the cage executes the oloid movement.

14. The method of claim 1, whereby the container of step a) is exactly the final container of the pharmaceutical composition, which is used for the application to a patient, without any other components.

15. A method of selecting a stable pharmaceutical composition comprising:
   a) providing a number of liquid pharmaceutical compositions in a number of containers,
   b) moving one or more of the said containers in an oloid movement in three dimensions (x, y and z), wherein the oloid movement results in an increased turbidity of the liquid pharmaceutical compositions in the one or more of the said containers, and wherein the increased turbidity is higher than a turbidity that would be produced by horizontal shaking of the container for a same amount of time,
   c) determining the stability of said liquid pharmaceutical compositions after shaking, and
   d) selecting a stable liquid pharmaceutical composition.

16. The method of claim 15, whereby the number of liquid pharmaceutical compositions tested in step a) is the same as the number of containers in step a) and/or whereby the number of liquid pharmaceutical compositions tested in step a) is at least 20, 50, 96, 100, 200, 384, 500 or 1000.

* * * * *

UNITED STATES PATENT AND TRADEMARK OFFICE
CERTIFICATE OF CORRECTION

PATENT NO. : 9,753,021 B2  
APPLICATION NO. : 14/381697  
DATED : September 5, 2017  
INVENTOR(S) : Patrick Garidel, Thomas Hennes and Torsten Schultz-Fademrecht Page 1 of 1

It is certified that error appears in the above-identified patent and that said Letters Patent is hereby corrected as shown below:

In the Specification

Column 13, Table 2, in the heading row Batch No.:  
IgG4_F5 should be changed to --IgG4_F4--;  
IgG4_F6 should be changed to --IgG4_F5--; and  
IgG4_F7 should be changed to --IgG4_F6--.

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*